US00PP16708P2

(12) United States Plant Patent

Fell, Jr.

(10) Patent No.: US PP16,708 P2

(45) Date of Patent: Jun. 20, 2006

(54) *VRIESEA* PLANT NAMED 'VRSP100'

(50) Latin Name: *Vriesea splendens*
Varietal Denomination: VRSP100

(76) Inventor: David N. Fell, Jr., 2191 Ainaola Dr., Hilo, HI (US) 96720

( * ) Notice: Subject to any disclaimer, the term of this patent is extended or adjusted under 35 U.S.C. 154(b) by 54 days.

(21) Appl. No.: 11/022,035

(22) Filed: Dec. 24, 2004

(51) Int. Cl.
*A01H 5/00* (2006.01)

(52) U.S. Cl. ..... Plt./370

(58) Field of Classification Search ..... Plt./370
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Vriesea* plant named 'VRSP100', characterized by its compact and upright plant habit; attractive foliage with distinct contrasting light green and dabrk green crossbands and random spots; relatively short leaves arranged in a dense rosettes; and upright and long non-branching inflorescences with conspicuous bright red-colored flower bracts.

3 Drawing Sheets

Botanical designation: *Vriesea splendens.*
Cultivar denomination: 'VRSP100'.

BACKGROUND OF THE INVENTION

The present Invention relates to a new and distinct cultivar of *Vriesea* plant, botanically known as *Vriesea splendens,* and hereinafter referred to by the cultivar name 'VRSP100'.

The new *Vriesea* is a product of a planned breeding program conducted by the Inventor in Honolulu and Hilo, Hi. The objective of the breeding program is to develop compact *Vrieseas* with attractive foliage and inflorescences.

The new *Vriesea* originated from a chance self-pollination in Honolulu, Hi. of the *Vriesea splendens* cultivar Myer's Favorite, not patented. The cultivar VRSP100 was discovered and selected by the Inventor as a flowering plant within the progeny of the stated self-pollination in a controlled environment in Hilo, Hi. in March, 1991.

Asexual reproduction of the new cultivar by divisions in Hilo, Hi., since October, 1991, has shown that the unique features of this new *Vriesea* are stable and reproduced true to type in successive generations.

SUMMARY OF THE INVENTION

Plants of the cultivar VRSP100 have not been observed under all possible environmental conditions. The phenotype may vary somewhat with variations in environment and culture such as temperature and light intensity without, however, any variance in genotype.

The following traits have been repeatedly observed and are determined to be the unique characteristics of 'VRSP100'. These characteristics in combination distinguish 'VRSP100' as a new and distinct cultivar of *Vriesea:*

1. Compact and upright plant habit.
2. Attractive foliage with distinct contrasting light green and dark green crossbands and random spots; relatively short leaves arranged in a dense rosettes.
3. Upright and long non-branching inflorescences with conspicuous bright red-colored flower bracts.

Plants of the new *Vriesea* are most similar to plants of the parent, the cultivar Myer's Favorite, however plants of the new *Vriesea* differ primarily from plants of the cultivar Myer's Favorite in plant habit and leaf length as plants of the new *Vriesea* are more compact and have shorter leaves than plants of the cultivar Myer's Favorite.

Plants of the new *Vriesea* can be compared to plants of the *Vriesea* cultivar Fire, not patented. However, in side-by-side comparisons conducted by the Inventor in Hilo, Hi., plants of the new *Vriesea* differed from plants of the cultivar Fire primarily in foliage luster and coloration as plants of the cultivar Fire had dull foliage with less color contrast between the crossbands, spots and ground color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Vriesea.*

The photograph on the first sheet comprises a side perspective view of a typical container of 'VRSP100' with three flowering plants per container.

The photograph on the second sheet comprises a close-up view of typical plants of 'VRSP100' with a developing inflorescence (left) and a fully developed inflorescence (right). The photograph on the third page is a side perspective view of a typical non-flowering plant of 'VRSP100' (left) and 'Myer's Favorite' (right) showing the differences in plant habit and leaf length.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following description were grown with three plants per 15-cm container in a polyethylene-covered greenhouse in Hilo, Hi. during the autumn. During the production of the plants, day temperatures ranged from 20 to 30° C., night temperatures ranged from 17 to 20° C. and light levels ranged from 6,000 to 8,000 footcandles. Plants were about 15 months old when the photograph and description were taken.

Botanical classification: *Vriesea splendens* cultivar VRSP100.

Parentage: Self-pollination of *Vriesea splendens* cultivar Myer's Favorite, not patented.

Propagation:

*Type.*—By divisions.

*Time to initiate roots, summer.*—About 30 days at 28° C.

*Time to initiate roots, winter.*—About 45 days at 25° C.

*Root description.*—Fibrous, fine; brown in color.

*Rooting habit.*—Freely branching.

Plant description:

*Form.*—Compact and upright plant habit; inverted triangle; symmetrical. Short internodes; dense and bushy rosette of stiff leaves; leaves, relatively short.

*Plant height (soil level to top of foliar plane).*—About 28 cm.

*Plant height (soil level to top of inflorescences).*—About 57 cm.

*Plant diameter.*—About 43 cm.

*Vigor.*—Moderately vigorous.

*Foliage description.*—Arrangement/appearance: Rosette; short internodes; relatively short leaf length; distinct contrasting light green-colored ground color and dark green-colored crossbands and random spots. Length: About 22.5 cm. Width: About 3.7 cm. Shape: Linear. Apex: Aristate. Base: Clasping. Margin: Entire. Texture, upper and lower surfaces: Smooth, glabrous; leathery. Luster, upper and lower surfaces: Somewhat glossy. Aspect: Concave; apex recurved. Venation pattern: Parallel. Color: Developing and fully expanded leaves, upper surface: Ground color, close to 191A; crossbands and random spots, darker green than 147A; towards the apex, close to 187A. Developing and fully expanded leaves, lower surface: Ground color, close to 189A to more green than 189A; crossbands and random spots, more purple than 200A. Veins, upper and lower surfaces: Same as lamina.

Inflorescence description:

*Inflorescence form.*—Upright and long non-branching inflorescences; flowers subtended by conspicuous imbricate flower bracts; inflorescences supported on erect and strong scapes.

*Quantity of inflorescences.*—Typically one per plant.

*Inflorescence longevity.*—Inflorescences of the new *Vriesea* are very long-lasting; flower bract coloration is maintained for about two months. Inflorescences persistent.

*Natural flowering season and time to flower.*—Plants flower throughout the year and begin to flower about 15 months after planting.

*Scape description.*—Length: About 57 cm. Diameter: About 6 mm. Internode length: About 2.4 cm. Aspect: Erect. Strength: Strong. Texture: Smooth. Color: Close to 155A.

*Flowers.*—Quantity per inflorescence: About 14 flowers and flower buds. Corolla: Arrangement: Three petals, gameopetalous. Length: About 2.2 cm. Width: About 6 mm. Shape: Narrowly deltoid. Apex: Acuminate. Base: Clasping. Margin: Entire. Texture, inner and outer surfaces: Smooth, glabrous; waxy. Color, inner and outer surfaces: Close to 12A. Calyx: Arrangement: Three petals, gameosepalous. Length: About 2.4 cm. Width: About 7 mm. Shape: Narrowly deltoid. Apex: Acuminate. Base: Clasping. Margin: Entire. Texture, inner and outer surfaces: Smooth, glabrous; waxy. Color, inner and outer surfaces: Close to 155B. Reproductive organs: Stamens: Quantity per flower: Six. Filament length: About 9 mm. Anther length: About 8.5 mm. Anther color: 17A. Pollen: None observed. Pistils: Pistil length: About 2.2 cm. Style length: About 1.5 cm. Style color: Closest to 187A. Ovary: Superior with three locules. Length: About 7.5 mm. Color: Close to 187A.

*Seed/fruit.*—Seed and fruit production has not been observed.

*Flower bracts.*—Arrangement: Arranged in closely-spaced vertical ranks along the inflorescence; two-ranked. Quantity per inflorescence: About 14. Shape: Deltoid. Apex: Acuminate to cuspidate. Base: Clasping. Margin: Entire. Texture, upper and lower surfaces: Smooth, glabrous; waxy. Length: About 6.5 cm. Width: About 2.8 cm. Texture, upper and lower surfaces; Smooth, glabrous; waxy. Color: When developing, inner and outer surfaces: Close to 144A to 144B. Fully opened, inner surface: Close to 150D. Fully opened, outer surface: Close to 44A.

*Scape bracts.*—Arrangement: Arranged in closely-spaced vertical ranks along the inflorescence; two-ranked. Quantity per inflorescence: About ten. Shape: Deltoid. Apex: Aristate. Base: Clasping. Margin: Entire. Texture, upper and lower surfaces: Smooth, glabrous; waxy. Length: About 4.4 cm. Width: About 2.4 cm. Texture, upper and lower surfaces: Smooth, glabrous; waxy. Color: When developing and fully developed, inner surface: Close to 147A to 147B. When developing and fully opened, outer surface: Close to 146A; crossbands and random spots, more purple than 200A.

Temperature tolerance: Plants of the new *Vriesea* have been observed to tolerate temperatures from about 5 to 40° C.

Diseases/pest resistance: Plants of the new *Vriesea* have not been observed to resistant to pathogens and pests common to *Vriesea*.

It is claimed:

1. A new and distinct cultivar of *Vriesea* plant named 'VRSP100', as illustrated and described.

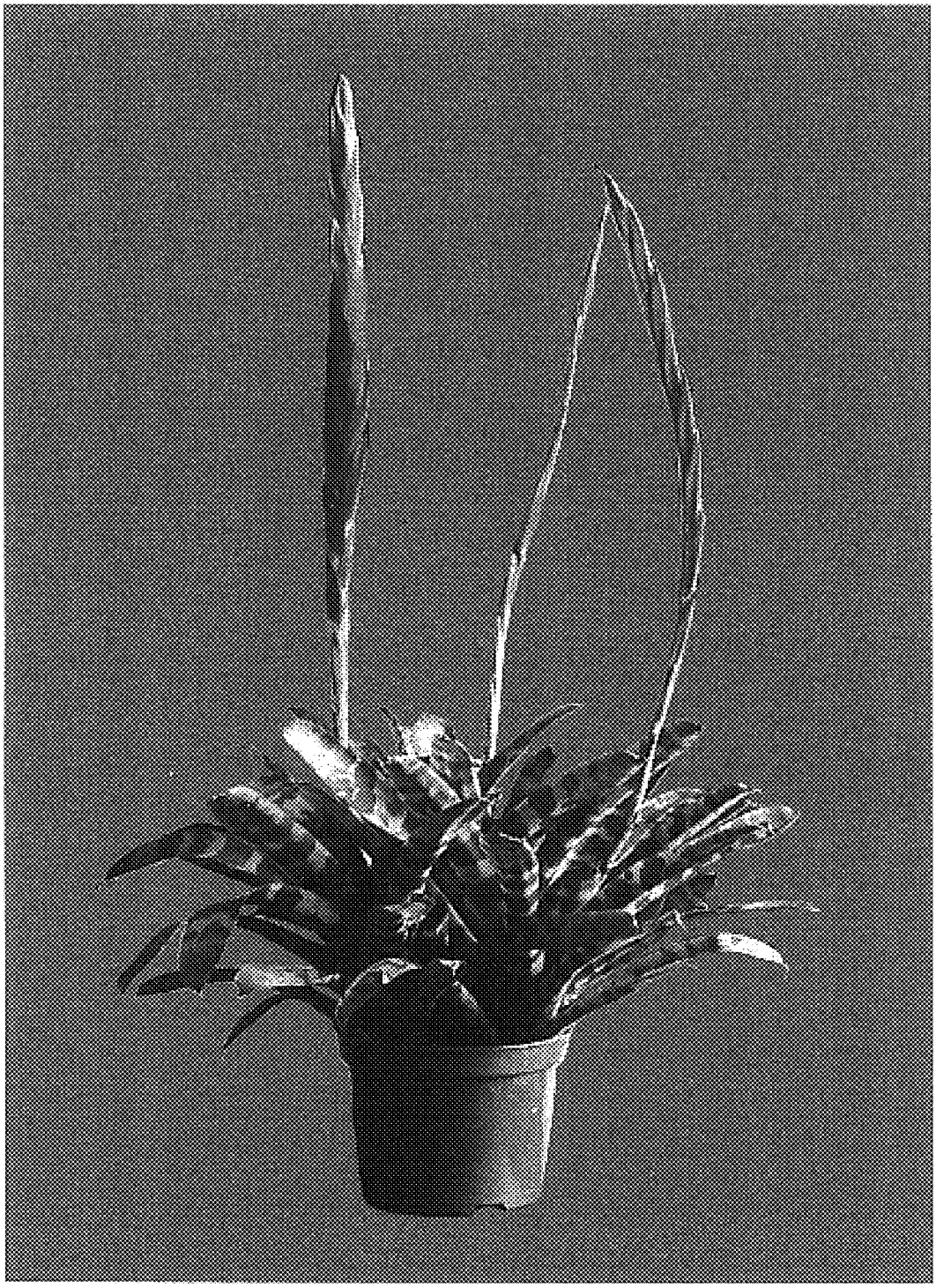

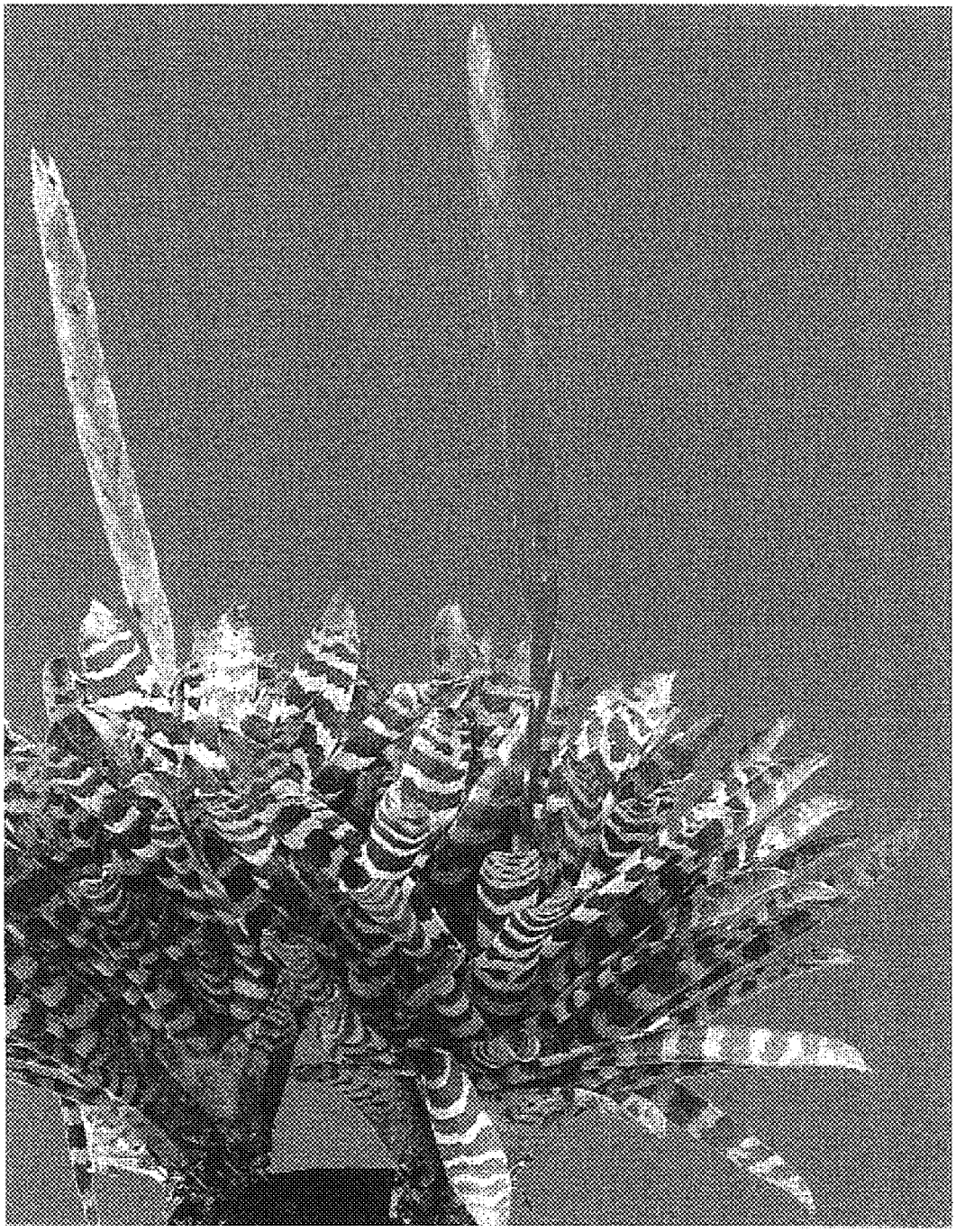

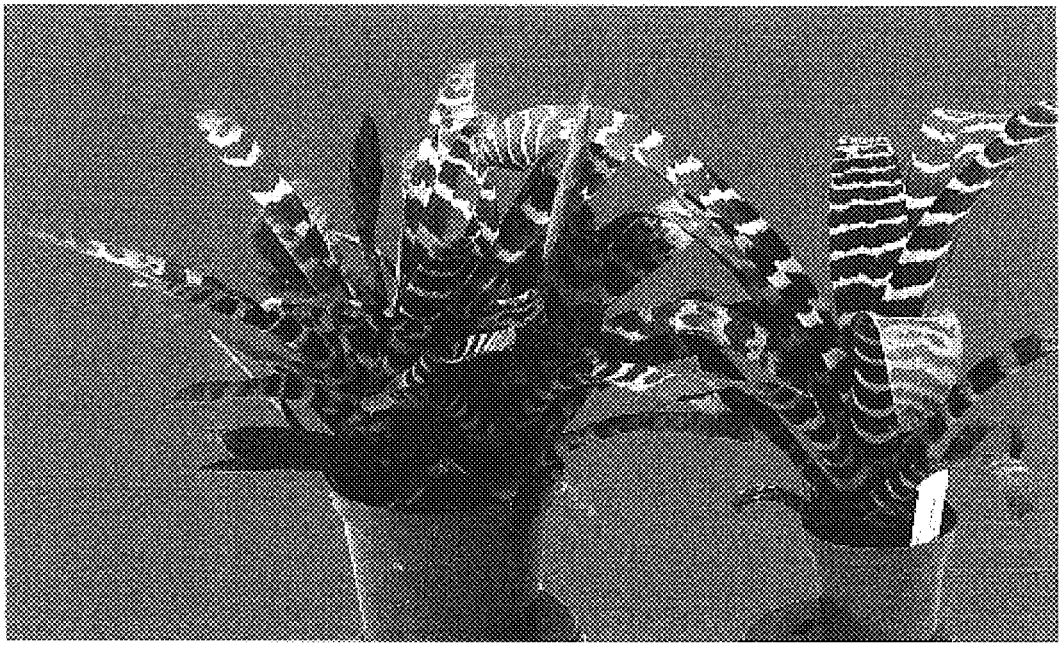

* * * * *